(12) United States Patent
Kong et al.

(10) Patent No.: US 10,030,253 B2
(45) Date of Patent: Jul. 24, 2018

(54) MICROFLUIDIC-BASED GENE SYNTHESIS

(71) Applicants: David Kong, Lexington, MA (US); Peter A. Carr, Medford, MA (US); Joseph M. Jacobson, Newton, MA (US)

(72) Inventors: David Kong, Lexington, MA (US); Peter A. Carr, Medford, MA (US); Joseph M. Jacobson, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 67 days.

(21) Appl. No.: 14/529,080

(22) Filed: Oct. 30, 2014

(65) Prior Publication Data

US 2015/0064791 A1     Mar. 5, 2015

Related U.S. Application Data

(63) Continuation of application No. 11/751,604, filed on May 21, 2007, now abandoned.

(51) Int. Cl.
| | |
|---|---|
| *C12Q 1/68* | (2018.01) |
| *C12N 15/90* | (2006.01) |
| *C12P 19/34* | (2006.01) |
| *C12N 15/70* | (2006.01) |

(52) U.S. Cl.
CPC ........... *C12N 15/902* (2013.01); *C12N 15/70* (2013.01); *C12P 19/34* (2013.01)

(58) Field of Classification Search
CPC .......... C12Q 1/68; C07H 21/02; C40B 40/06; G01N 33/48
See application file for complete search history.

(56) References Cited

U.S. PATENT DOCUMENTS

2003/0224521 A1* 12/2003 Court ................. A01K 67/0275
                                                                435/455
2004/0171154 A1*  9/2004 Storici ................. C12N 15/102
                                                                435/455

FOREIGN PATENT DOCUMENTS

WO        WO02/062988        * 8/2002

OTHER PUBLICATIONS

Zhou et al, Microfluidic PicoArray synthesis of oligodeoxynucleotides and simultaneous assembling of multiple DNA sequences, 2004, Nucleic Acids Research, 32, 5409-5417.*

* cited by examiner

*Primary Examiner* — Narayan Bhat
(74) *Attorney, Agent, or Firm* — Norma E. Henderson

(57) ABSTRACT

A method for synthesizing long DNA constructs from oligonucleotide precursors directly within a microfluidic device uses several oligonucleotides at once. A precursor mix containing at least two oligonucleotide precursors with at least partial base complementarity is introduced into an input of a microfluidic chip and at least one cycle of at least one gene synthesis protocol is applied to fabricate a DNA construct containing the sequence of at least two oligonucleotide precursors. A method for the synthesis of a modified DNA construct includes electroporating at least one oligonucleotide encoding for at least one point mutation and having homology with at least one DNA region of a target cell into the target cell and incorporating the oligonucleotide into the target cell DNA through the action of recombination protein beta or a recombination protein beta functional homolog.

9 Claims, 9 Drawing Sheets

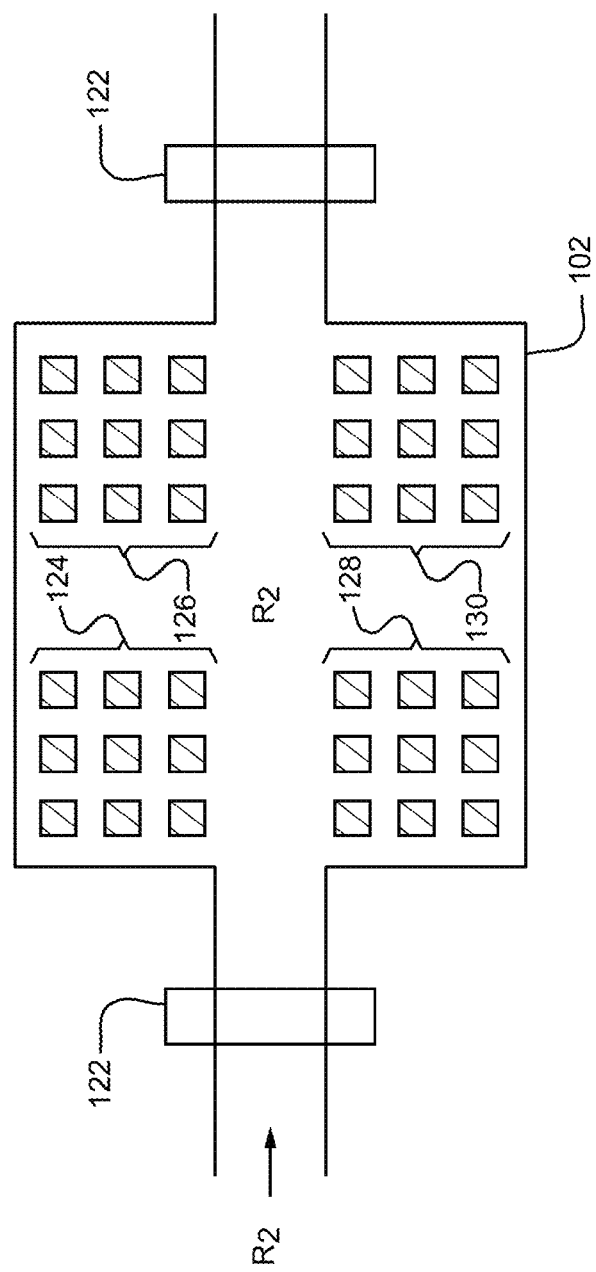

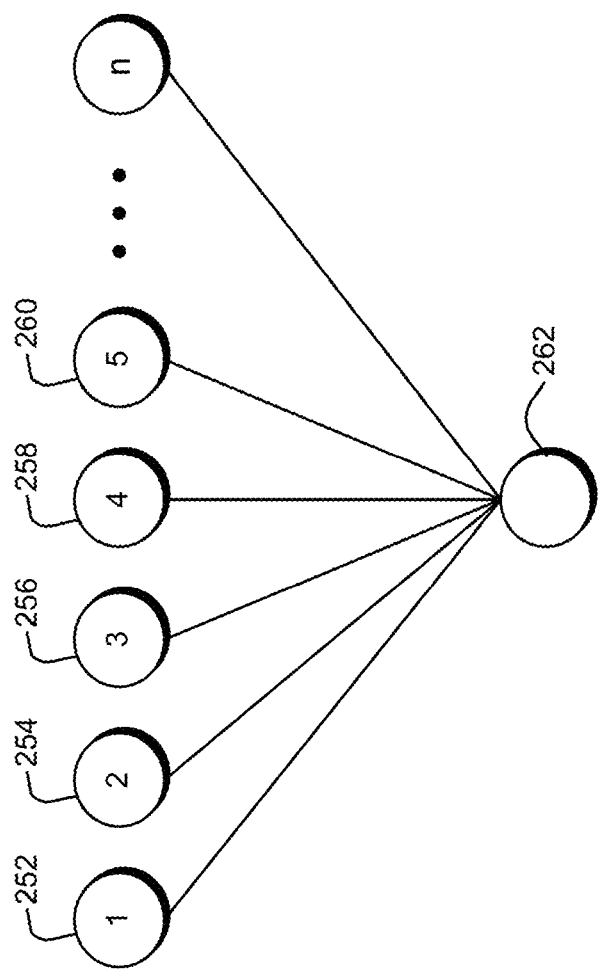

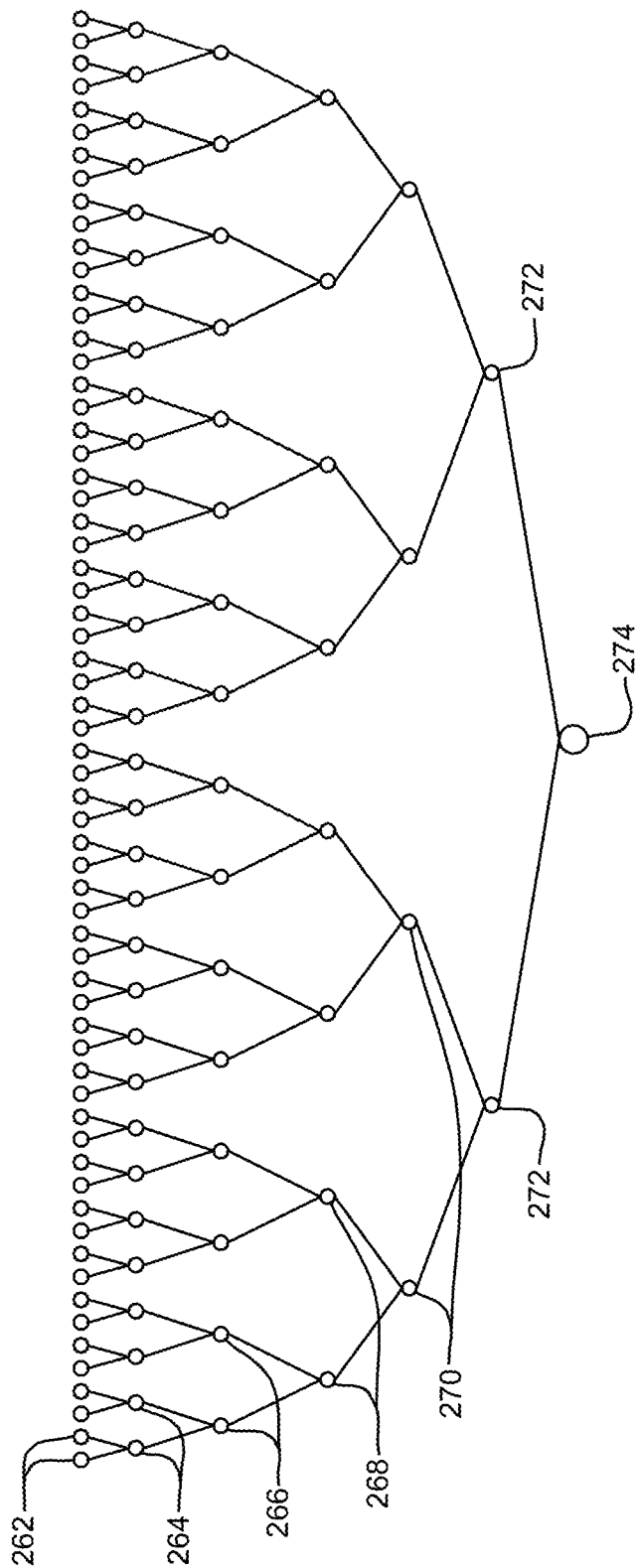

MICROFLUIDIC-BASED GENE SYNTHESIS

RELATED APPLICATIONS

This application is a continuation of U.S. patent application Ser. No. 11/751,604, filed May 21, 2007, now abandoned, which claims the benefit of U.S. Provisional Application Ser. No. 60/801,812, filed May 19, 2006, the entire disclosures of which are herein incorporated by reference.

STATEMENT REGARDING FEDERALLY SPONSORED RESEARCH OR DEVELOPMENT

This invention was made with U.S. government support under Grant Number CCR-0122419, awarded by the National Science Foundation. The government has certain rights in this invention.

FIELD OF THE TECHNOLOGY

The present invention relates to gene synthesis and, in particular, to methods for the direct synthesis of a gene, genes, gene systems, or long DNA constructs from oligonucleotide precursors within a microfluidic device.

BACKGROUND

A great proportion of the activity and expenditure in the field of molecular biology is devoted to the isolation, modification, and expression of genes (sequences of nucleotides ranging from ~400 bases to ~several kilobases) and DNA constructs (e.g. gene systems, such as metabolic pathways and other long DNA constructs, ranging from several Kb to ~300 Kb) for a range of applications, including the production of protein-based drugs, the production of chemicals and biofuels, and the creation of protein libraries, gene knockouts, and other mutations and modifications aimed at garnering a fundamental understanding of molecular biology.

Although it has been feasible for some time to synthesize small genes (<1 Kb) ab initio from synthetic oligonucleotides (i.e. sequences of DNA up to ~100 nucleotide bases) [e.g. Gupta et al., *Proc Natl Acad Sci*, 57, 148 (1968); Stemmer et al., Gene, 164, 49 (1995)], the cost and error rate associated with this procedure has been limiting in terms of the size gene or the size of the gene library that can economically be synthesized. Recent advances in the use of DNA oligonucleotide microarray-based methods for synthesizing the synthetic oligonucleotide precursors [e.g. Tian et. al., *Nature*, 432, 1050 (2004); Zhou et al., *Nucleic Acids Res*, 32, 5409 (2004); Richmond et al., *Nucleic Acids Res*, 32, 5011], as well as error correcting methods [e.g. Carr et. al., *Nucleic Acids Res*, 32, e162 (2004); Tian et. al., *Nature*, 432, 1050 (2004)] for assembling such oligonucleotides into genes or larger DNA constructs, coupled with the vast sequence knowledge that has been accumulated through genome sequencing projects, have opened up the new possibility of 'bit to gene', in which a gene or other DNA construct can be downloaded or designed in silico and then directly synthesized. However, such procedures still involve macroscopic liquid volumes (typically greater than 1 microliter and as much as milliliters) and macroscopic fluid handling, which typically requires costly robotic handlers. In the case of microarray-derived oligonucleotide precursors, these precursors also require amplification, which introduces errors. Thus, the overall cost and time currently associated with synthesizing gene-length and longer DNA constructs (e.g. bacterial genomes) are prohibitive to widespread use and availability.

Court et al. have previously disclosed methods for inducing homologous combination using single-stranded nucleic acids [U.S. Pat. App. Pub. No. 2005/0079618; Court et al., Apr. 14, 2005] and, in Ellis et al., *Proc Natl. Acad. Sci.* USA 98:6742-6, 2001, single oligonucleotides have been employed to modify a genome, but these procedures do not solve these problems. What has been needed, therefore, is the ability to make several changes at once, so that gene-length and longer DNA constructs may be fabricated in a time and cost-effective manner.

SUMMARY

The present invention is a method for synthesizing genes, systems of genes, and other long DNA constructs from oligonucleotide precursors directly within a microfluidic device. It permits several changes to be made at once by using several oligonucleotides at once. Use of the present invention keeps fluid volumes small (typically less than 1 uL), obviates the need for most robotics, and permits gene synthesis from oligonucleotide precursors without requiring an initial amplification of such nucleotides.

In one aspect, the present invention is a method to fabricate genes (~400 bases to several kilobases), longer DNA constructs (from several kilobases to several hundred kilobases), and gene libraries directly within a microfluidic device. In another aspect, the present invention provides methods for the sequential assembly of genes that scale in assembly time proportional to gene length, as well as hierarchical assembly methods that scale logarithmically in gene length. In still another aspect, the present invention provides means for directly coupling a DNA oligonucleotide microarray to the gene synthesis microfluidic device, which are capable in combination of going directly from bits (design of the gene on computer) to physical DNA constructs without any macroscopic sample handling and without requiring the intervening amplification of oligonucleotides.

In one aspect of the present invention, a precursor mix containing at least two oligonucleotide precursors with at least partial base complementarity is introduced into an input of a microfluidic chip and at least one means of oligonucleotide cleavage and at least one cycle of at least one gene synthesis protocol are applied to fabricate a DNA construct containing the sequence of at least two oligonucleotide precursors. In a preferred embodiment of this aspect, the means of oligonucleotide cleavage comprises at least polymerase and gene synthesis protocol comprises applying a time varying thermal field to the precursor mix to fabricate the DNA construct. Alternatively, a force is applied to move the precursor mix relative to a spatial thermal gradient. In another embodiment, the precursor mix contains at least ligase and the gene synthesis protocol comprises containing the mix for an effective incubation time.

In another aspect of the present invention, a method for the synthesis of a modified DNA construct includes electroporating at least one oligonucleotide encoding for at least one point mutation and having homology with at least one DNA region of a target cell into the target cell and incorporating the oligonucleotide into the target cell DNA through the action of recombination protein beta or a recombination protein beta functional homolog.

BRIEF DESCRIPTION OF THE DRAWINGS

Other aspects, advantages and novel features of the invention will become more apparent from the following detailed description of the invention when considered in conjunction with the accompanying drawings wherein:

FIG. 1B is a schematic representation of an example embodiment of a fluidic chamber enclosing a set of spots of oligonucleotides that are utilized as building blocks for synthesizing multiple genes or arbitrary DNA constructs simultaneously according to another aspect of the present invention;

FIG. 2B is a schematic representation of an example embodiment of a fluidic architecture whereby n DNA fragments are assembled into a larger DNA construct in a single stage according to the present invention;

FIG. 2C is a schematic representation of an example embodiment of a fluidic architecture employing multiple stages of hierarchical gene synthesis according to the present invention;

DETAILED DESCRIPTION

Figure 1A:
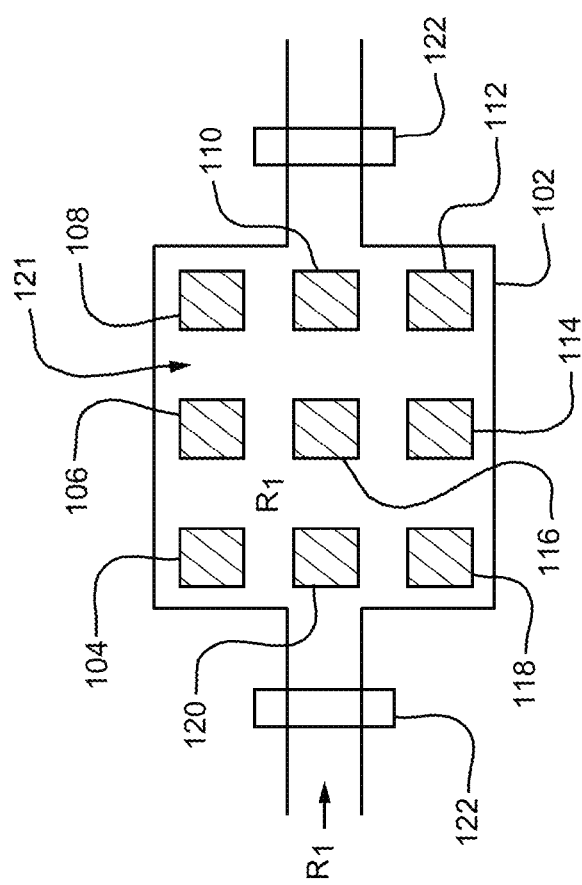
FIG. 1A is a schematic representation of an example embodiment of a fluidic chamber enclosing a set of spots of oligonucleotides that are utilized as building blocks for synthesizing a single gene or other arbitrary DNA construct according to one aspect of the present invention.

The present invention is a set of preferred methods and microfluidic designs wherein microfluidic chips are employed for the synthesis of genes and other DNA constructs. Embodiments include the use of DNA oligonucleotide microarrays in conjunction with a microfluidic device for use in the synthesis of genes and other DNA constructs. Additional on-chip processes according to the present invention include on-chip error correction and transcription and translation of the DNA gene into a protein gene product.

As used herein, the following terms expressly include, but are not to be limited to:

"DNA tile set" means a group of polynucleotide components arranged into a specified spatial pattern.

"DNA oligonucleotide microarray" means a solid substrate that is typically composed of glass, but could be composed of silicon, PDMS, or a variety of other materials, which has arrayed on its surface a multitude of oligonucleotide sequences, and wherein each sequence is confined to specific, user-designed areas. For each given area, or 'oligonucleotide spot' which is associated with a given oligonucleotide sequence, a large ensemble of DNA molecules of that sequence (typically $10^6$-$10^{10}$ molecules) is present. A microarray can be composed of as many as hundreds of thousands of discrete oligonucleotide spots. The terms "DNA oligonucleotide microarray", "microarray", "array", and "microarray chip" are used interchangeably.

"Electroporation" means the use of time-varying electric fields to allow molecules outside a cell to penetrate the interior of a cell. In the context of the invention, electroporation is used to cause oligonucleotides to enter cells.

"Error correction" means removal of flawed, corrupt, or otherwise undesired components from a larger set. In the context of the invention, DNA error correction refers to the reduction of undesired polynucleotide components, such as by removing them from a pool of molecules or by altering the flawed molecules to produce the desired ones.

"Microfluidic chip" means a device for manipulating nanoliter to microliter volumes of liquid. Such devices frequently contain features such as channels, chambers, and/or valves, and can be fabricated from a variety of different materials, including, but not limited to, glass and polydimethylsiloxane (PDMS). More complex versions of these devices are sometimes referred to as a "lab on a chip" reflecting the integration of several functions in one device. The terms 'microfluidic chip' and 'microfluidic device' are used interchangeably.

"Oligonucleotide precursor" means a polynucleotide used as a component to produce a larger polynucleotide. An example would be a 50-mer deoxyribonucleotide used as a component to produce a 500 base pair DNA construct.

"Precursor mix" means a combination of two or more oligonucleotide precursors.

"Recombination protein beta" means the beta protein from bacteriophage lambda, or its functional equivalents/homologs (for example, E. coli protein RecT). These proteins are capable of mediating various types of recombination processes.

"Shotgun gene (or genome) modification" means the process of using multiple oligonucleotides to direct the in vivo modification of DNA molecules. For example, two oligonucleotides can be electroporated into a cell, and each oligonucleotide can direct the modification of a different region of the chromosomal DNA. This usage is distinct from multisite site-directed mutagenesis, which in the art refers to making multiple modifications to a DNA molecule in vitro, typically in a highly purified system.

Single Chamber Microfluidic Gene Synthesis Systems.

In a first preferred embodiment, a microfluidic gene synthesis system according to the present invention comprises a single microfluidic chamber. FIG. 1A is a schematic representation of an example embodiment of a fluidic chamber enclosing a set of spots of oligonucleotides that are utilized as building blocks for synthesizing a single gene or other arbitrary DNA construct. In FIG. 1A, fluidic chamber 102 is aligned to enclose oligonucleotide spots 104, 106, 108, 110, 112, 114, 116, 118, 120. Each of these oligonucleotide spots, typically deployed on an oligonucleotide or DNA array chip 121, is typically composed of $10^6$-$10^{10}$ individual oligonucleotides of a given sequence. Each sequence is designed such that the ensemble of molecules, represented in FIG. 1A by 9 distinct oligonucleotides, will assemble into a desired gene or other arbitrary DNA construct in the presence of the appropriate enzyme (for example, but not limited to, DNA polymerase) and other reagents operating under the appropriate gene synthesis protocols (for example, but not limited to, polymerase assembly multiplexing), as is well known in the art of de novo gene synthesis.

The device shown in FIG. 1A is operated as follows. First, a reaction mixture, R1, containing reagents, such as DNA polymerase, MlyI restriction enzyme (for enzymatic cleavage), dNTPs, primers, Polymerase Chain Reaction (PCR) buffer, and 0.1% n-dodecyl-beta-D-maltoside, or other suitable reagent mixtures known in the art, is loaded into chamber 102 with valves 122 open. Once loaded, valves 122 are closed, thus enclosing the reaction mixture and oligonucleotide spots in a single volume. Typical volumes are in the tens and hundreds of nL, though smaller and larger fluid volumes are possible. Next, the temperature of the fluid volume is elevated so that the restriction enzyme is active, thus enabling cleavage of oligonucleotides 104, 106, 108, 110, 112, 114, 116, 118, 120 from microarray surface 121. Upon achieving oligonucleotide release, the fluid volume is then thermocycled according to standard PCR protocols (such as, but not limited to, 94° C. for 30 seconds for dehybridization, 55° C. for 30 seconds for annealing, 72° C. for 60 seconds for annealing, for a total of 45 cycles) to achieve full synthesis of the desired double-stranded DNA molecules with sequence information defined by oligonucleotides 104, 106, 108, 110, 112, 114, 116, 118, 120.

The discussion of the operation of the embodiment of FIG. 1A assumes that oligonucleotides from the oligonucleotide spots are cleaved enzymatically from the surface, as is well known in that art of gene synthesis from oligonucleotide arrays. Examples of such enzymatic cleavage include, but are not limited to, the use of restriction enzymes such as MlyI, or other enzymes or combinations of enzymes capable of cleaving single or double-stranded DNA such as, but not limited to, Uracil DNA glycosylase (UDG) and DNA Endonuclease IV. Other means of cleavage known in the art may also be advantageously employed in the present invention, including, but not limited to, chemical (base labile) cleavage of DNA molecules or optical (photolabile) cleavage from the surface. PCR can also be employed to generate building material for gene synthesis by copying the oligonucleotides while they are still anchored to the microarray.

FIG. 1B is a schematic representation of an example embodiment of a fluidic chamber enclosing a set of spots of oligonucleotides that are utilized as building blocks for synthesizing multiple genes or arbitrary DNA constructs simultaneously. In FIG. 1B, single chamber 102 encloses four sets of oligonucleotide spots 124, 126, 128, 130, each of which comprises oligonucleotides capable of assembling into four distinct genes or other arbitrary DNA molecules. In this embodiment, reaction mixture R2, containing similar reagents to mixture R1 of FIG. 1A but with the exception of having different primers, is introduced into chamber 102, and valves 122 are closed to isolate a single reaction volume containing R2 and the various oligonucleotide spots. A temperature regimen similar to that employed in conjunction with the embodiment of FIG. 1A is employed to cleave the oligonucleotides and synthesize multiple genes or other arbitrary DNA molecules in a single chamber.

Multiple Chamber (Hierarchical) Microfluidic Gene Synthesis Systems.

A second preferred embodiment of the present invention comprises multiple chamber (hierarchical) microfluidic gene synthesis systems. Although single chambers are a good choice for short DNA constructs, limits exist in terms of the maximum number of oligonucleotides that can be assembled within a single reaction chamber system, which consequently limits the size of the largest possible DNA construct capable of being synthesized in a single chamber. One solution to this problem is to utilize a hierarchical approach for DNA synthesis wherein, in order to synthesize a "large" desired construct, multiple "small" DNA segments are synthesized in parallel in separate chambers and then introduced into a subsequent chamber where, after mixing with fresh reagents to replace those consumed in the initial reactions, such as, but not limited to, polymerase and dNTPs, the larger desired DNA molecule is then assembled.

Figure 2A:
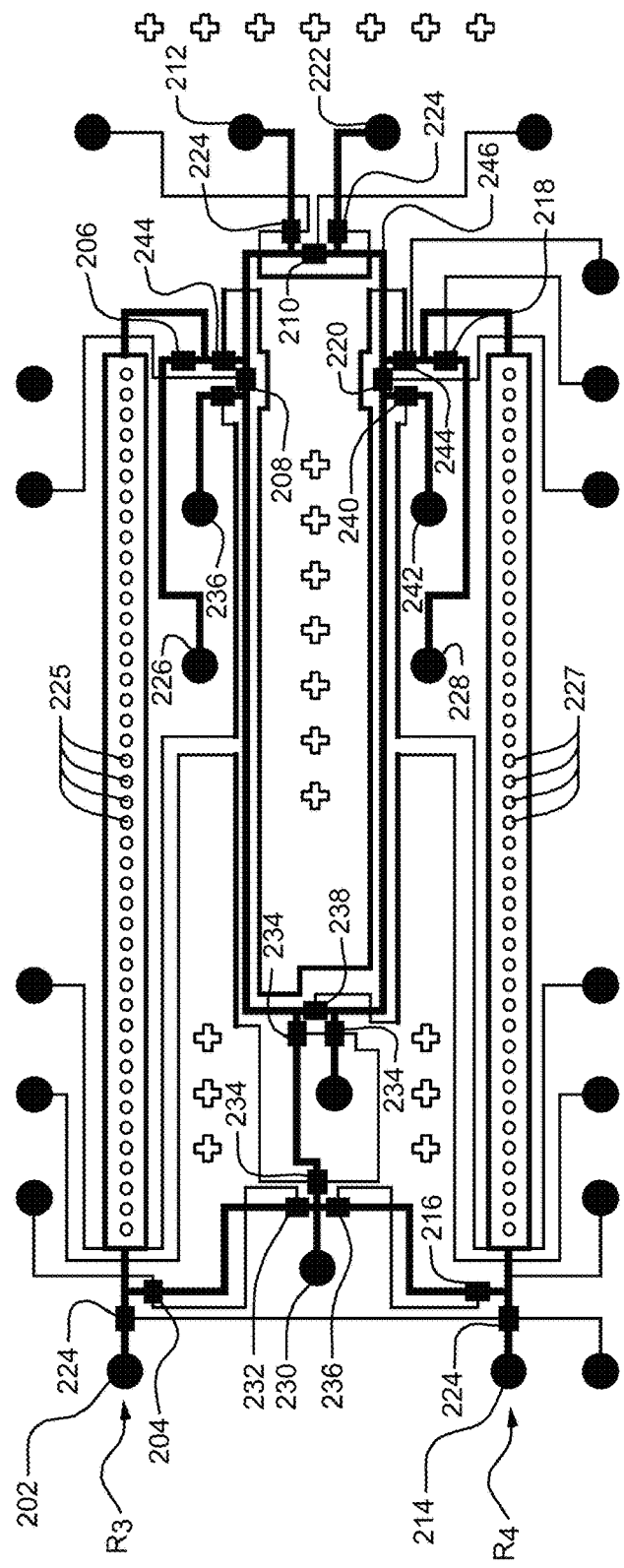
FIG. 2A is a schematic representation of an example embodiment of a fluidic architecture for single-stage hierarchical gene synthesis according to the present invention.

An exemplary device capable of synthesizing a desired gene from two gene segments 1 and 2, respectively, is shown in FIG. 2A, which is is a schematic representation of an exemplary fluidic architecture for single-stage hierarchical gene synthesis. In the embodiment of FIG. 2A, reaction mix R3, containing the necessary reagents for oligonucleotide cleavage and gene synthesis of gene segment 1, is introduced into inlet 202 into a reaction volume defined by valves 204, 206, 208, 210, which are closed, with R3 exiting through outlet port 212. Similarly, mix R4, containing the necessary reagents for oligonucleotide cleavage and gene synthesis of gene segment 2, is introduced into inlet 214 into a volume defined by valves 216, 218, 220, 210, which are also closed, with R4 exiting through outlet port 222. Next, valves 224 are closed shut to seal reaction mixtures R3 and R4 into isolated volumes, whereupon the device temperature is controlled to activate enzymatic cleavage of the sets of oligonucleotide spots 225, 227.

Once cleaved, the reaction mixtures are thermocycled, preferably in parallel, in order to achieve synthesis of gene segments 1 and 2. The thermocycled reaction mixes R3 and R4, now containing assembled gene segments 1 and 2, can then be collected through outlet ports 226, 228, respectively, by opening valves 206, 218 and introducing pressurized air, water, or other collection buffer through inlet 230 with valve 232 open and valve 234 closed. Next, reaction mix R5, containing a fresh supply of polymerase, dNTPs, primers, and other necessary reagents, is introduced through inlet 236, with valve 234 still closed and valves 238, 240 open, with R5 exiting through outlet 242. Once R5 has been introduced into the fluidic, valves 208, 210, 220 are opened with valves 240, 244, 224, 234 being closed, thus bringing R3 and R4, both containing gene segments 1 and 2, into contact with R5. Valves 208, 210, 220 are then actuated and employed as a peristaltic pump, pushing the three fluid segments through rectangular loop 246 until a homogeneous mixture is achieved. Upon completion of mixing, this new mixture is then thermocycled, thus assembling the desired full-length gene. The solution containing this gene can be retrieved by introducing pressurized air, water, or other buffer through inlet 230 with valve 232 closed, valve 234 open, and valve 238 closed, with the remaining valves maintaining their previous configurations.

Many variations upon the method of hierarchical gene synthesis of the present invention are possible and are within the scope of the present invention. For instance, for single-stage assemblies, such as the one shown in FIG. 2A, instead of combining two gene segments, multiple chambers synthesizing n gene segments can be combined in a similar fashion to assemble a large DNA construct. This is depicted in FIG. 2B, which is a schematic representation of an embodiment of a fluidic architecture wherein n DNA fragments are assembled into a larger DNA construct in a single stage. In FIG. 2B, chambers 252, 254, 256, 258, 260, up to chamber n, contain distinct DNA segments that, when introduced into chamber 262, are combined to yield the desired construct comprised of the various gene segments in the previous hierarchy level.

Furthermore, multiple stages of assembly are possible. This is illustrated in FIG. 2C, which is a schematic representation of an exemplary embodiment of a fluidic architecture employing multiple stages of hierarchical gene synthesis. As depicted in FIG. 2C, seven successive thermocycling reactions are conducted to assemble 64 gene segments in chambers 262 to ultimately produce a final desired product in chamber 274. Specifically, upon completion of the 64 individual segments in chambers 262, the products are then fed to chambers 264, whereupon they are combined into 32 gene segments, whose products are then fed into chambers 266, and so on, through chambers 268, 270, 272, until the final full-length product is synthesized in chamber 274.

In the preceding discussion for both single chamber and multiple chamber microfluidic gene synthesis systems, in a preferred embodiment the oligonucleotide spots are prepared by means of oligonucleotide or DNA chip array synthesis, as is well known in the art (e.g. Affymetrix, Combimatrix). In order for the oligonucleotides deployed on the surface of such a DNA array chip to serve as the oligonucleotide spots employed in the present invention, the oligonucleotide array chip should ideally be interfaced to the microfluidic chamber. This fluidic-microarray interfacing can be achieved by a variety of methods, including, but not limited to, pressure-bonding or adhesive-bonding. In the case of pressure-bonding, force is applied to sandwich the microarray and fluidic together sufficiently to prevent the leakage of fluid from the channels or other device features while the fluids are being manipulated. In the case of adhesive-bonding, a patterned adhesive of some kind such as, but not limited to, a double-sided adhesive that has been patterned with a laser, is used to bond the fluidic surface to the microarray surface. In other preferred embodiments, materials such as, but not limited to, CYTOP, a fluoropolymer, parylene, a vapor-deposited polymer, or poly(dimethylsiloxane) (PDMS), a silicone-based elastomer, can be utilized as the adhesive material. Again, the bonding must be sufficient to prevent the leakage of fluid from channels or other device features while the fluids are being manipulated. Additionally, bonding between the fluidic and the microarray must occur with appropriate registration, so that features on the microarray, specifically the oligonucleotide spots but also potentially other features, are properly aligned to the desired features of the fluidic device.

It is necessary in general to control the temperature of the fluidic device, and subsequently any fluid volumes within a device, in order to facilitate the necessary chemical and biological processes. The method for temperature control in the preferred embodiment involves placing the hybrid fluidic-microarray device onto a thermal heating block, for example a standard PCR thermocycler with in situ adapter, but any of the methods known in the art would be suitable and may be advantageously employed in the present invention.

Protein Synthesis.

Figure 3:
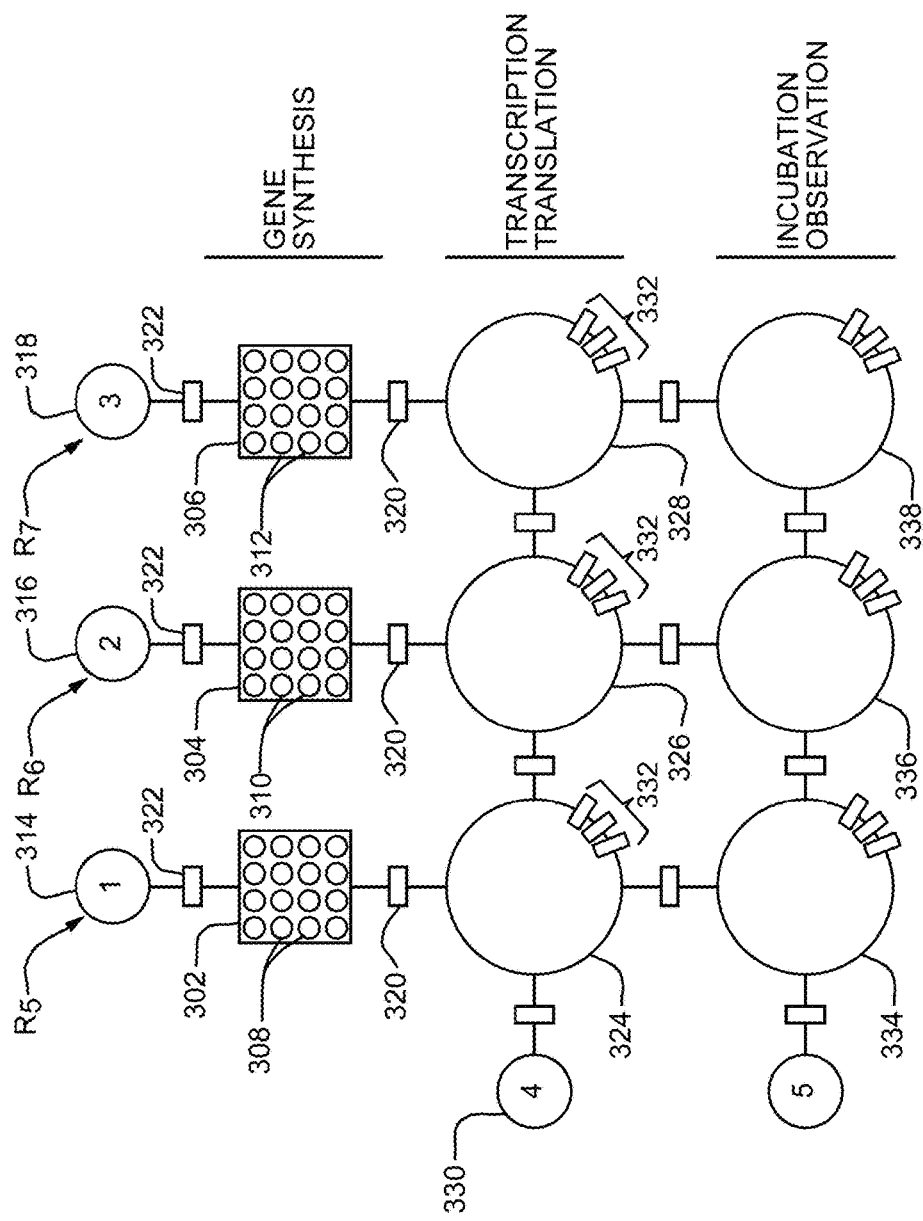
FIG. 3 is a schematic representation of an example embodiment of a fluidic architecture according to the present invention wherein, upon completion of parallel gene synthesis, the synthesized genes are subsequently expressed in vitro.

Recently it has been demonstrated that proteins can be expressed in cell-free environments, such as a microfluidic volume, by employing commercially available in vitro transcription/translation mixtures [Tabuchi et al., *Proteomics* 2, 430 (2002)]. Such a capability can readily be coupled with the described gene synthesis protocols. FIG. 3 is a schematic representation of an embodiment of a fluidic architecture according to the present invention where, upon completion of parallel gene synthesis, the synthesized genes are subsequently expressed in vitro. As shown in FIG. 3, chambers 302, 304, 306 contain sets of oligonucleotides 308, 310, 312, that represent three distinct genes when assembled. Reaction mixtures R5, R6, and R7, containing the necessary reagents to cleave and assemble the three sets of oligonucleotides, are introduced through inlets 314, 316, 318 by compacting against valve 320. Once loaded, valve 322 is closed to isolate the fluid volumes for thermocycling and gene synthesis. Once assembled, the three reaction mixtures are then introduced into mixing chambers 324, 326, 328, whereupon they are combined with in vitro transcription/translation mixtures introduced through inlet 330. Mixing valves 332 are then employed to mix the gene segments with the in vitro transcription/translation mix and, after incubating at the appropriate temperature, transcription and translation occur. The expressed proteins are then pushed to chambers 334, 336, 338 for observation. As shown in FIG. 3, the expressed proteins of the example shown are capable of fluorescing red, yellow, and green (e.g. DsRed, YFP, and GFP).

On-chip Electroporation and Shotgun Gene Modification.

A further preferred embodiment of the present invention comprises a microfluidic system capable of bringing about a large number of simultaneous point mutations within a target genome by means of electroporating a pool of N oligonucleotides into a cell, each oligonucleotide coding for a point mutation, coupled with a mechanism for recombining the oligonucleotides with corresponding homologous regions of the cell's genome or other genetic material. In an example employing this embodiment, there are N regions of a genome to be homologously recombined with N oligonucleotides, each coding for a different mutation that it is desired to introduce. If the efficiency of each individual recombination event is given by ε, then the probability of swapping out any one region after R attempts (e.g. after R repeated electroporation cycles) is given by $P_1=1-(1-\varepsilon)^R$, and the corresponding probability of the original sequence remaining after R tries is $P_0=(1-\varepsilon)^R$. If swapping operations are independent from each other, then the overall probability of swapping out at least $M_0$ regions after R tries is given by:

$$P_{SUM} = \sum_{M=M_0}^{N} \frac{N!}{M!(N-M)!} P_1^M P_0^{N-M}$$

Using this relation, it can be shown that, for a fixed R (i.e. fixed number of attempted insertion cycles (e.g. electroporation cycles)), there exists a threshold value for ε, $\varepsilon_{Threshold}$, above which it becomes efficient to carry out shotgun modification.

Figure 4:
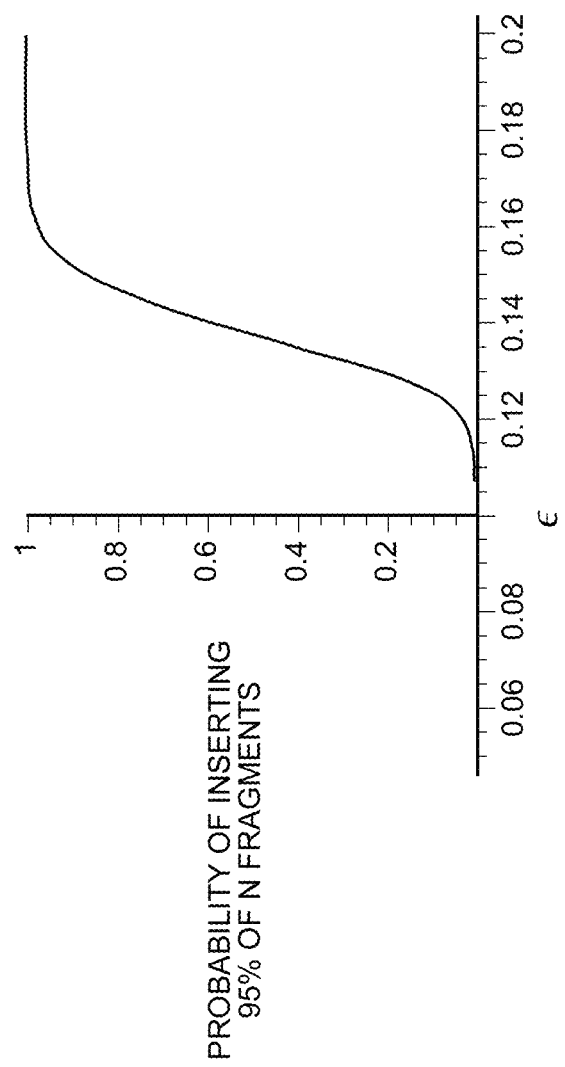
FIG. 4 is a graphical representation of the probability fabricating clones containing 95% of N inserts as a function of insertion probability for an example embodiment of a system, according to an aspect of the present invention, undergoing 20 insertion cycles.

FIG. 4 is a graphical representation of the probability of fabricating clones containing 95% of N inserts as a function of insertion probability for a system undergoing 20 insertion cycles according to this aspect of the present invention. If $M_0$ is set to 95% of N (e.g., if N=326, then $M_0$=310) then we have for small R approximately:

$$\varepsilon_{Threshold} \sim 10 e^{-5\sqrt{\sqrt{80R}}}$$

for a method of shotgun modification. Table 1 shows (using the exact expression) the number of insertion cycles R as a function of insertion efficiency, ε, required to guarantee that 50% of clones will contain 95% or more of the desired N regions.

TABLE 1

| ε | R |
|---|---|
| .92 | 1 |
| .71 | 2 |
| .39 | 5 |
| .22 | 10 |
| .025 | 100 |
| .01 | 290 |
| .001 | 2900 |

A preferred embodiment for carrying out the shotgun modification procedure according to this aspect of the present invention comprises a microfluidic system that includes electroporation means, as known in the art, and that takes as input a pool of N oligonucleotides with homology to the regions of the existing genetic material of a cell, further encoding N mutations that it is desired to introduce, and cells containing the recombination protein beta or a functional homolog thereof. The oligonucleotides permeate the cell by means of electroporation and are incorporated into the native cell's genetic material by the beta protein mechanism, as described by Ellis et al., *Proc Natl. Acad. Sci.* USA 98:6742-6, 2001. As shown previously, if ε exceeds $\varepsilon_{Threshold}$, then repeated electroporations of the oligonucleotide will converge such that the majority of the cells will contain a preponderance of the desired point mutations.

A simple example of the results of shotgun modification is shown in Table 2. A modified strain of *E. coli* MG1655 bearing the beta gene under control of a heat-sensitive repressor was induced to produce beta protein, and treated to make electrocompetent as common to the art. A mixture of three distinct oligonucleotides was transported into the cell culture by electroporation, and the chromosomes of the cells were modified by these oligonucleotides. In this example, each of the three oligonucleotides encoded a point mutation that would restore function to a previously inactivated gene (for the antibiotic resistance marker genes kan, cat, and bla). Growth of the resulting cell culture and plating onto appropriate growth media with combinations of the appropriate antibiotics revealed the efficiencies with which cells underwent one, two, or three modifications.

TABLE 2

| | Cell sample 1 | Cell sample 2 |
|---|---|---|
| $Bla^R$ (single modification) | 10.2% | 9.3% |
| $Cat^R$ (single modification) | 19.9% | 12.6% |
| $Kan^R$ (single modification) | 15.1% | 18.6% |
| $Bla^R$ $Cat^R$ (double modification) | 1.9% | 1.7% |
| $Bla^R$ $Kan^R$ (double modification) | 3.1% | 4.3% |
| $Cat^R$ $Kan^R$ (double modification) | 3.6% | 3.9% |
| $Bla^R$ $Cat^R$ $Kan^R$ (triple modification) | 0.55% | 0.54% |

Another embodiment of the invention is designed to produce the desired oligonucleotides in vivo using a specially designed DNA construct, for example, but not limited to, a bacterial artificial chromosome (BAC). This construct contains the desired sequences encoding one or more such oligonucleotides, as desired for shotgun modification described above. One way to produce such single-stranded oligonucleotides is to employ promoter and transcription terminator elements to first generate a RNA version of the desired oligonucleotide, followed by reverse transcription to generate complementary a DNA-RNA hybrid, followed by digestion of the RNA strand. A plurality of such elements would be encoded in BAC form. The advantage of such an approach is that the DNA construct generated in vitro only needs to be electroporated once. Following electroporation, production of the desired oligonucleotide (or oligonucleotides) would proceed in vivo, followed by action of beta protein or a functional homolog to incorporate the encoded change (or changes) into the host chromosome. This process may proceed continually simply by allowing the cells to grow in continuous culture, until reaching the point where the desired changes are achieved.

On-chip Error Correction by Hybridization by Selection.

Another preferred embodiment of the present invention is a microfluidic gene synthesis system that includes on-board error correction. It has been shown that errors in gene synthesis can be substantially reduced by purifying oligonucleotide building blocks prior to synthesis. In particular, a process known as hybridization by selection [Tian et al., *Nature* 432:1050-4, 2004] can be employed within a microfluidic chip, wherein oligonucleotides released from the microarray are hybridized to oligonucleotides containing complementary sequences, followed by washing and elution of non-hybridized oligonucleotides [Tian et. al., *Nature,* 432, 1050 (2004)]. By repeating this process for multiple cycles, error-free oligonucleotides can be preferentially retained, thus enabling the synthesis of DNA constructs with fewer errors.

Figure 5:
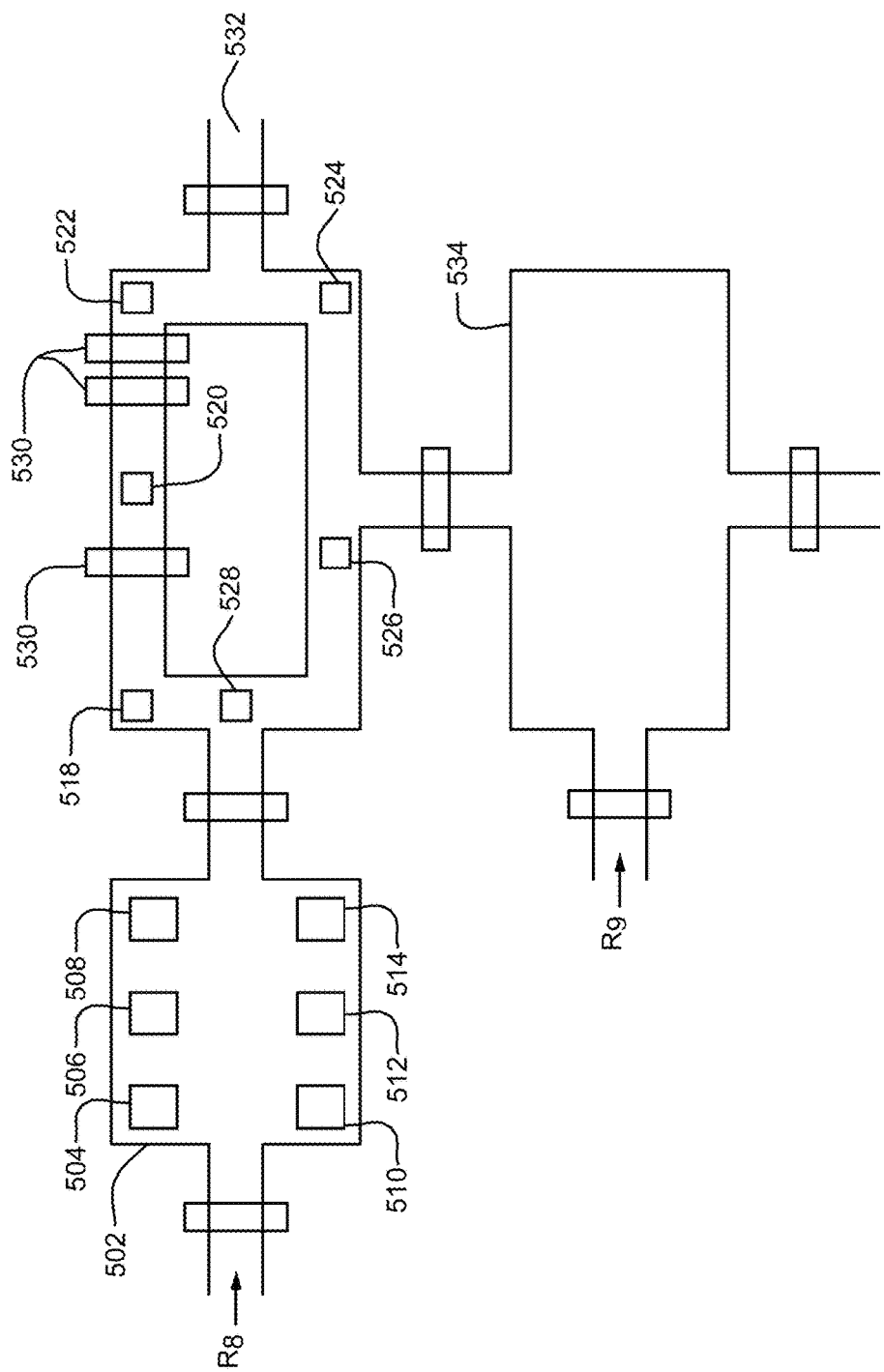
FIG. 5 is a schematic representation of an example embodiment of on-chip hybridization by selection according to one aspect of the present invention.

This process is shown in FIG. 5, which is a schematic representation of an embodiment of on-chip hybridization by selection, according to one aspect of the present invention, wherein, upon release from the chip, oligonucleotides in solution are hybridized to spots of oligonucleotides containing complementary sequences, followed by washing and elution of non-hybridized oligonucleotides. This is repeated for multiple cycles, facilitating the preferential selection of error-free oligonucleotides for DNA synthesis. In FIG. 5, reaction mixture R8, containing only reagents necessary for oligonucleotide cleavage, is introduced into chamber 502, whereupon oligonucleotides 504, 506, 508, 510, 512, 514 are released from the surface of the microarray. The mixture containing these oligonucleotides is then pushed into mixing chamber 516, which encloses oligonucleotide spots 518, 520, 522, 524, 526, 528, which are complementary to oligonucleotides 504, 506, 508, 510, 512, 514. The reaction mixture temperature is then set to ideal conditions for annealing to occur, at which point mixing valves 530 are employed to circulate the released oligonucleotides over their anchored complementary counterparts, thus facilitating rapid hybridization.

Once hybridized, oligonucleotides that are not hybridized, and thus are likely to contain mutations, are then eluted out of outlet 532. This process is repeated for multiple cycles, at which point the temperature of the reaction mixture is raised so that the preferentially retained oligonucleotides de-hybridize. They are then pushed into reaction chamber 534, whereupon reaction mixture R9, containing the necessary reagents for gene synthesis, is introduced. Thermocycling is then conducted to synthesize the desired DNA construct from relatively error-free oligonucleotide building blocks. Again, it should be noted that, in other preferred embodiments, reaction mixture R8 may alternatively already contain oligonucleotides 518, 520, 522, 524, 526, and 528, thus eliminating the need for cleavage of oligonucleotides or a microarray substrate.

In a preferred embodiment, the microfluidic devices shown in FIGS. 1A-B, 2A-C, 3, and 5, which contain within them various chambers, channels, and valves, are composed of a polymeric material such as, but not limited to, PDMS, a silicone-based elastomer, and are constructed by methods of fabrication well known in the art of multi-layer soft lithography. The microfluidic device could also be composed of other polymeric materials, including, but not limited to, polyethylene, polypropylene, and polymethylmethacrylate. Hard materials including, but not limited to, glass and silicon can also be employed, and these can be machined via methods well-known to those skilled in the art of microfabrication. Furthermore, the microfluidic chamber and all connected channels that will contact reaction mixtures may optionally be coated with additional materials including, but not limited to, CYTOP, a fluoropolymer, or parylene, a vapor deposited polymer. Such coatings can be achieved via methods well-known to those skilled in the art of microfabrication. In a preferred embodiment, the valves shown in FIGS. 1A-B, 2A-C, 3, and 5 are fabricated and operated via methods known to those skilled in the art of multilayer soft lithography [e.g. Unger, et al. *Science,* 288, 113 (2000)] or similar valving technologies, utilizing polymeric materials such as, but not limited to, PDMS in combination with hard materials such as, but not limited to, glass [e.g. Grover, *Sensors and Actuators B,* 89, 315 (2003)].

In other preferred embodiments, instead of cleaving oligonucleotides from the surface of the microarray, oligonucleotides may alternatively be introduced in the reaction mixtures. For example, in FIG. 1A, oligonucleotides 104, 106, 108, 110, 112, 114, 116, 118, 120 can already be present in reaction mixture R1 at the appropriate concentration (e.g. 25 nM each), thus enabling synthesis of the desired gene without a microarray. In such an embodiment, the "floor" of the microfluidic chamber may be composed of a variety of materials including, but not limited to, glass, silicon, PDMS, CYTOP, or parylene, and does not require the presence of oligonucleotides on the surface of the reaction chamber floor. Similarly, for the embodiments described in FIGS. 1B, 2A-C, and 3, the oligonucleotides may also be introduced in the reaction mixtures, thus not requiring the presence of the oligonucleotide spots shown.

Figure 6:
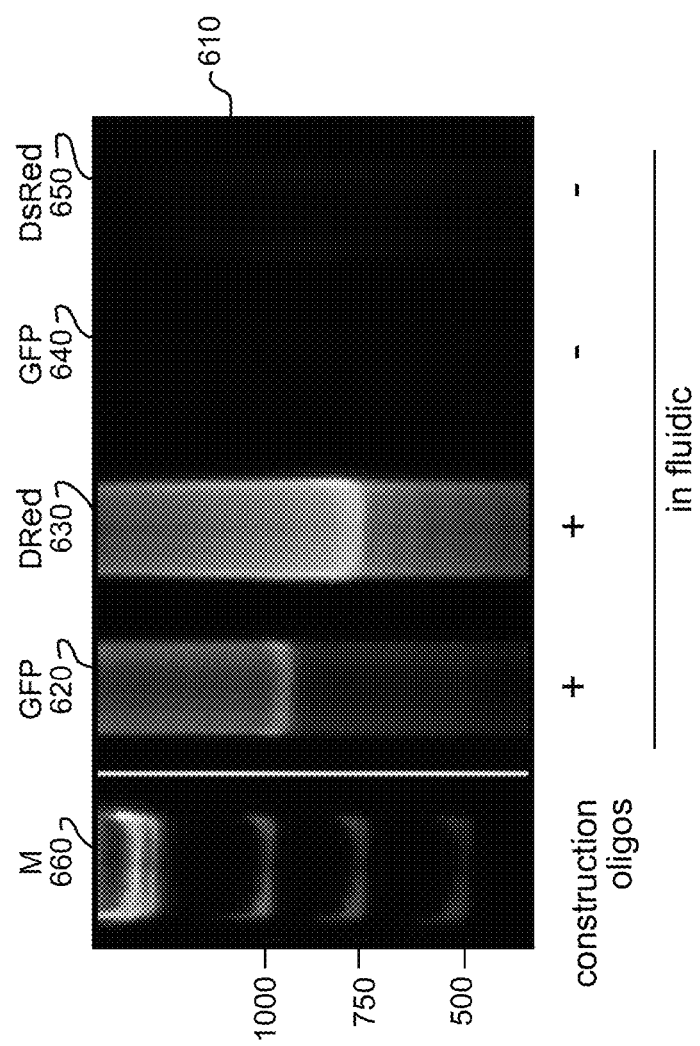
FIG. 6 is a polyacrylamide gel electrophoresis (PAGE) showing successful parallel synthesis of genes along with negative controls in multiple chambers, according to an aspect of the present invention.

FIG. 6 is a polyacrylamide gel electrophoresis (PAGE) image showing successful parallel synthesis of genes along with negative controls in multiple chambers. In FIG. 6, gel image 610 verifies the synthesis of GFP 620 and DsRed 630 DNA constructs by the method of the present invention, wherein 42 and 26 oligonucleotides, respectively, were included in the reaction mixture and assembled, in parallel, in two chambers of a microfluidic device. Gel 610 also depicts successful negative controls 640, 650, wherein reaction mixtures that did not contain a complete set of oligonucleotides were thermocycled in parallel in separate chambers, thus experiencing the same temperature gradients, did not yield the desired DNA constructs. In the presence of construction oligonucleotides, DNA constructs GFP and dsRed (993 and 733 by respectively) and OR128-1 and ble (942 and 461 by respectively) are synthesized and amplified. Without construction oligonucleotides, no product bands are generated. Molecular weight markers 660 (M) are also shown, with 500, 750, and 1000 by positions indicated.

While a preferred embodiment of the present invention is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. A method for the synthesis of a modified DNA construct comprising the steps of:
electroporating a pool of oligonucleotides into at least one target cell, wherein the pool of oligonucleotides comprises at least two different types of oligonucleotides such that each different type of oligonucleotide in the pool has homology with a different DNA region of the target cell than the DNA regions with which the other types of oligonucleotides have homology and each different type of oligonucleotide encodes for a different point mutation than the point mutations encoded for by the other types of oligonucleotides; and
simultaneously incorporating, in a single step, the electroporated oligonucleotides into the target cell DNA through the action of recombination protein beta or a recombination protein beta functional homolog, simultaneously bringing about a plurality of simultaneous point mutations within the target cell, wherein at least two of the simultaneous point mutations are of different types,
wherein the steps of electroporating and incorporating are carried out entirely within a microfluidic chip, the microfluidic chip comprising a microfluidic device having a fluidic architecture configured for implementing the steps of electroporating and incorporating.

2. The method of claim 1, wherein the step of electroporating is repeated a plurality of times using a plurality of oligonucleotide pools.

3. The method of claim 1, comprising steps for hierarchical assembly of the oligonucleotides in the pool, comprising:
synthesizing small oligonucleotide segments in parallel in separate microfluidic chambers;
introducing the synthesized small oligonucleotide segments into a subsequent chamber; and
assembling the oligonucleotides,
wherein the microfluidic chambers and the subsequent chamber are contained on one or more microfluidic chips.

4. The method of claim 1, further comprising the step of applying at least one form of error correction.

5. The method of claim 4, wherein the error correction comprises at least one cycle of hybridization by selection and is carried out within the microfluidic system.

6. A method for the synthesis of a modified DNA construct, comprising the steps of:
introducing, into at least one target cell, at least one polynucleotide construct having homology with a plurality of DNA regions of the target cell and encoding for a plurality of different point mutations;
generating, using the polynucleotide construct, a plurality of oligonucleotides within the target cell, wherein the plurality of oligonucleotides comprises at least two different types of oligonucleotides such that each different type of oligonucleotide within the target cell has homology with a different DNA region of the target cell than the DNA regions with which the other types of oligonucleotides have homology and each different type of oligonucleotide encodes for a different point mutation than the point mutations encoded for by the other types of oligonucleotides; and
simultaneously incorporating, in a single step, the oligonucleotides into the target cell DNA through the action of recombination protein beta or a recombination protein beta functional homolog, simultaneously bringing about a plurality of simultaneous point mutations within the target cell, wherein at least two of the simultaneous point mutations are different,
wherein the steps of introducing, generating, and incorporating are carried out entirely within a single microfluidic chip, the microfluidic chip comprising a microfluidic device having a fluidic architecture configured for implementing the steps of introducing, generating, and incorporating.

7. The method of claim 6, wherein the step of introducing is carried out through electroporation.

8. The method of claim 6, further comprising the step of applying at least one form of error correction.

9. The method of claim 8, wherein the error correction comprises at least one cycle of hybridization by selection and is carried out within the microfluidic system.

* * * * *